(12) United States Patent
Levenberg

(10) Patent No.: US 10,449,356 B2
(45) Date of Patent: Oct. 22, 2019

(54) INDUCING EMOTIONAL RESPONSE THROUGH CRANIOFACIAL STIMULATION

(71) Applicant: Abby D. Levenberg, New York, NY (US)

(72) Inventor: Abby D. Levenberg, New York, NY (US)

(73) Assignee: TREV Labs, LLC, Dover, DE (US)

( * ) Notice: Subject to any disclaimer, the term of this patent is extended or adjusted under 35 U.S.C. 154(b) by 0 days.

(21) Appl. No.: 15/960,227

(22) Filed: Apr. 23, 2018

(65) Prior Publication Data
US 2019/0232054 A1    Aug. 1, 2019

Related U.S. Application Data

(60) Provisional application No. 62/622,419, filed on Jan. 26, 2018.

(51) Int. Cl.
| | | |
|---|---|---|
| A61N 1/36 | (2006.01) | |
| A61N 1/04 | (2006.01) | |
| A61B 5/00 | (2006.01) | |
| A61B 5/16 | (2006.01) | |

(52) U.S. Cl.
CPC ......... *A61N 1/3603* (2017.08); *A61N 1/0472* (2013.01); *A61B 5/0077* (2013.01); *A61B 5/165* (2013.01); *A61B 5/4836* (2013.01); *A61N 1/36025* (2013.01)

(58) Field of Classification Search
CPC .............. A61N 1/3603; A61N 1/36025; A61N 1/0472; A61B 5/0077; A61B 5/165; A61B 5/4863
See application file for complete search history.

(56) References Cited

U.S. PATENT DOCUMENTS

| | | | |
|---|---|---|---|
| 9,440,070 B2 | 9/2016 | Goldwasser et al. | |
| 2007/0203539 A1* | 8/2007 | Stone | A61N 1/0529 607/59 |
| 2010/0114190 A1* | 5/2010 | Bendett | A61N 1/36014 607/3 |
| 2011/0026779 A1 | 2/2011 | Matsumoto et al. | |
| 2011/0115875 A1* | 5/2011 | Sadwick | H04N 7/15 348/14.08 |
| 2014/0277292 A1 | 9/2014 | Steel | |
| 2014/0277309 A1* | 9/2014 | Popovic | A61N 1/36096 607/115 |
| 2017/0135896 A1* | 5/2017 | Snow | A61H 23/0236 |

FOREIGN PATENT DOCUMENTS

WO    2018/045438 A1    3/2018

* cited by examiner

*Primary Examiner* — Paula J Stice

(74) *Attorney, Agent, or Firm* — Brian R. Galvin; Galvin Patent Law, LLC

(57) ABSTRACT

A system for inducing emotional response through craniofacial stimulation, comprising an emotion enhancement device that selects a stimulation configuration and directs the operation of a plurality of stimulation transducers based on the selected stimulation configuration. In some aspects the emotion enhancement device is configured to be worn on the head of a human user, and in some aspects the stimulation configuration is selected based on input cues from hardware sensors.

17 Claims, 16 Drawing Sheets

INDUCING EMOTIONAL RESPONSE THROUGH CRANIOFACIAL STIMULATION

CROSS-REFERENCE TO RELATED APPLICATIONS

This application claims benefit of, and priority to, U.S. provisional patent application Ser. No. 62/622,419, titled "DIRECTING EMOTIONAL RESPONSE THROUGH CRANIOFACIAL STIMULATION", which was filed on Jan. 26, 2018, the entire specifications of each of which are incorporated herein by reference.

BACKGROUND

Field of the Art

The disclosure relates to the field of human-computer interfaces, and more particularly to the field of electronic output for directly stimulating the human body.

Discussion of the State of the Art

In the field of human-computer interfaces, research is exploring the use of alternative interaction methods such as brainwave-driven control or neuromuscular input to operate computing devices, as well as output from computing devices using haptic and sensory feedback. This is particularly useful in biofeedback research and applications, where sensory output is used to assist a user in training or identifying specific physical or mental operations. A new use for alternative human-computer interaction involves using computer-driven output to stimulate the human body and elicit a specific response, effectively inverting the interaction and using the computer to aid or direct the physical or mental operation of the user. One example of this is the use of transcranial direct-current stimulation (tDCS), or transcranial magnetic stimulation (TMS), which may be used to alter the cognitive function of a user through electrical or magnetic stimulation, respectively.

However, existing applications are focused primarily on therapeutic uses for assisting with memory, depression, or other cognitive impairments, and are not suitable for active use by a user throughout their day. Existing applications also focus on specific areas of cognition or motor function, as with prosthetic devices that provide haptic feedback, and ignore the everyday use of emotional response that is a basic factor of human operation, despite growing evidence of the suitability of stimulation in directing a user's emotional state or eliciting a specific emotional response.

What is needed, is a means for eliciting or enhancing an emotional response in a user using non-invasive stimulation, that is suitable for casual use and is configured to assist the user in routine activities.

SUMMARY

Accordingly, the inventor has conceived and reduced to practice, a system and method for inducing emotional response through craniofacial stimulation, that uses non-invasive means to stimulate key areas of the face and head to elicit or heighten emotional response in a user.

In a typical embodiment, an emotional enhancement device is provided that may be equipped with a plurality of hardware sensors and hardware transducers. The sensors may be configured to receive a plurality of input cues such as sensing environmental cues, performing facial recognition and/or facial tracking, performing emotional response recognition, and the like. The transducers may be configured to target specific craniofacial emotion stimulation points to instill a specific emotional response based on a predefined configuration, or reactively apply emotional stimulation based in part on input cues received from the hardware sensors. The system may also be configured to utilize machine learning to analyze an emotion response, and adjust the sensors and transducers according to ensure the desired effect is attained.

According to one aspect, a system for inducing emotional response through craniofacial stimulation, comprising: an emotion enhancement device comprising at least a processor, a memory, and a plurality of programming instructions stored in the memory and operating on the processor, wherein the programming instructions, when operating on the processor, cause the processor to: select a stimulation configuration; select a plurality of target areas about a user's face and head based at least in part on the stimulation configuration; direct the operation of a plurality of stimulation transducers based at least in part on the stimulation configuration; and a plurality of stimulation transducers arranged about the emotion enhancement device, the plurality of stimulation transducers being arranged to correspond to a plurality of target areas about the face and head of a human user when the headwear is worn, wherein the plurality of stimulation transducers are configured to apply direct stimulation to the plurality of target areas, is disclosed.

According to another embodiment, the stimulation transducers comprise a laser emitter. According to another embodiment, the stimulation transducers comprise a light-emitting diode. According to another embodiment, the stimulation transducers comprise a motor. According to another embodiment, the stimulation transducers comprise an electrical contact.

According to another embodiment, the emotion enhancement device is configured to be worn on the face of a human user. According to another embodiment, the emotion enhancement device comprises a pair of glasses or goggles. According to another embodiment, the emotion enhancement device comprises a hat. According to another embodiment, the emotion enhancement device comprises a mask. According to another embodiment, the emotion enhancement device comprises a virtual reality headset.

According to another embodiment, the emotion enhancement device comprises room-installed transducer and sensor assemblies. According to another embodiment, the system further comprises a plurality of hardware sensors arranged about the emotion enhancement device, wherein the plurality of hardware sensors is configured to provide a plurality of sensor input cues to the processor. According to another embodiment, the stimulation configuration is selected based at least in part on the plurality of sensor input cues.

According to another aspect, a method for inducing emotional response through craniofacial stimulation, comprising the steps of: selecting, using an emotion enhancement device comprising at least a processor, a memory, and a plurality of programming instructions stored in the memory and operating on the processor, a stimulation configuration; selecting a plurality of target areas about a user's face and head based at least in part on the stimulation configuration; directing the operation of a plurality of stimulation transducers arranged about the item of headwear, the plurality of stimulation transducers being arranged to correspond to a plurality of target areas about the face and head of a human user when the headwear is worn, wherein the plurality of stimulation transducers are configured to apply direct stimulation to the plurality of target areas, based at least in part on the stimulation configuration; and applying stimulation to a plurality of target areas about a user's face and head, the target areas being selected based on the stimulation configuration, is disclosed.

According another aspect of the invention, a method for automated adjustment of a craniofacial stimulation emotional response is provided, comprising the steps of: (a) receiving a plurality of input cues from a plurality of hardware sensors positioned about an emotion enhancement device; (b) analyzing the input cues for at least emotional response intensity to craniofacial emotional stimulation using a facial tracking service; (c) adjusting a plurality of hardware transducers positioned about the emotion enhancement device based at least in part from the results of analysis of the input cues with an emotion response service; and (d) saving the adjustments in a data store for later recall.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
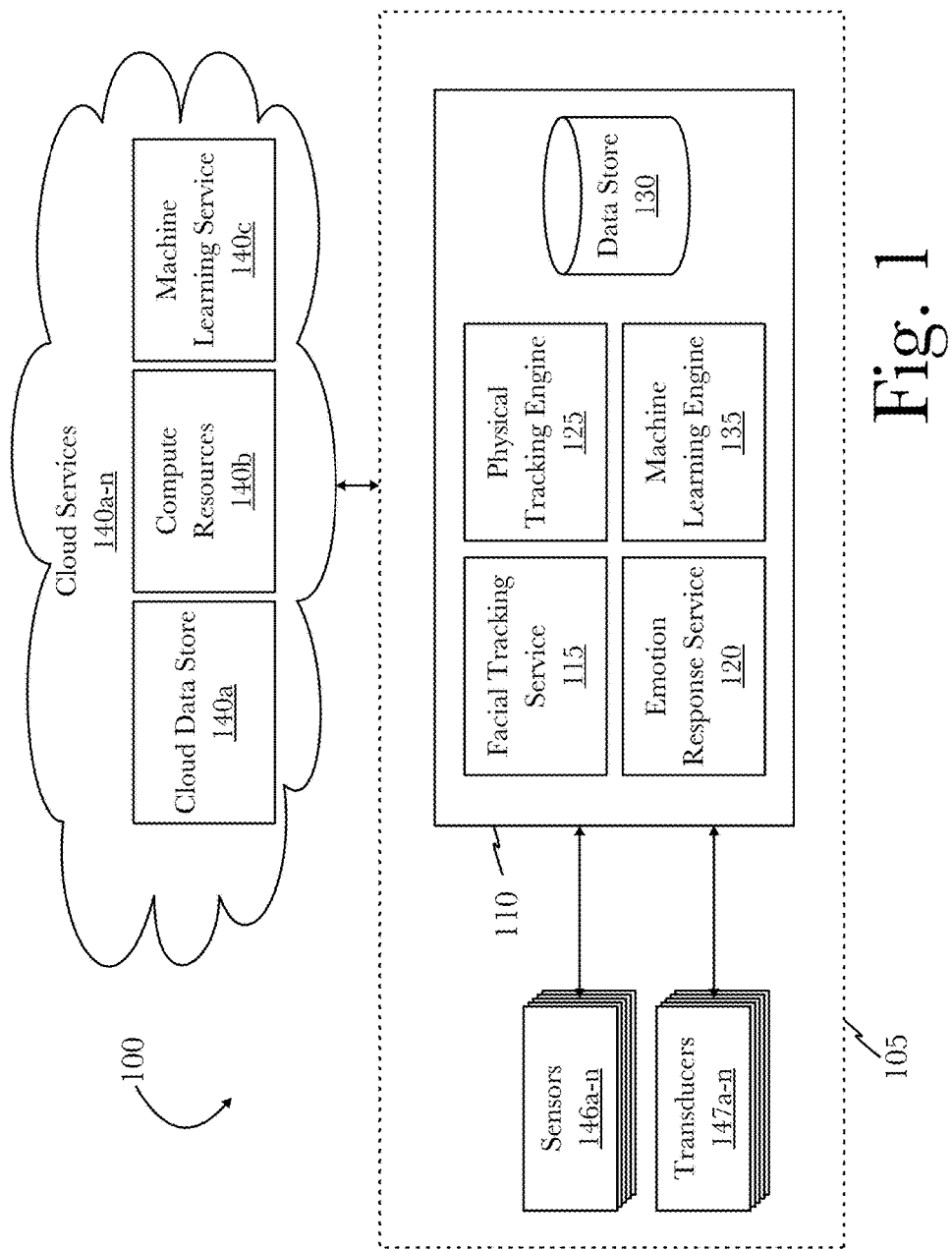
FIG. 1 is a block diagram of an exemplary system architecture of a system for inducing emotional response through craniofacial stimulation through the use of an emotional enhancement device, according to one aspect.

The inventor has conceived, and reduced to practice, a system and method for inducing emotional response through craniofacial stimulation, that uses non-invasive means to stimulate key areas of the face and head to elicit or heighten emotional response in a user.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Conceptual Architecture

FIG. 1 is a block diagram of an exemplary system architecture 100 of a system for inducing emotional response through craniofacial stimulation through the use of an emotional enhancement device 105, according to one aspect. According to the aspect, system architecture 100 may comprise an emotion enhancement device 105 (such as a computing device discussed below in FIGS. 13 and 16) configured to run a craniofacial emotional stimulation operating system 110. Emotion enhancement device 105 may connect with a plurality of cloud services 140a-n, and may comprise a plurality of sensors 146a-n and a plurality of transducers 147a-n. Connection to cloud services 140a-n may be conducted through a network connection, while connection to sensors 146a-n or transducers 147a-n may be a hard-wired, or may be wirelessly connected (for example via BLUETOOTH, WIFI, and the like). Some exemplary embodiments for device 105 are discussed in further detail below in FIGS. 3-6.

Operating system 110 may be configured to execute on a processor of a computer, embedded system, mobile device, system-on-a-chip, and the like to hand various functions pertaining to craniofacial emotional stimulation. Operating system 110 may comprise a facial tracking service 115, an emotion response service 120, a physical tracking engine 125, a machine learning engine 135, and a data store 130. Facial tracking service 115 may be configured to utilize machine learning engine 135 and sensors 146 to identify users, facial structure, current emotional state and intensity of said emotional state, and the like by, for example, performing a scan on a user's face using sensors 146a-n or transducers 147a-n. Facial tracking service 115 may also be configured to allow user-uploading of a photograph for analyzing with a facial recognition model by machine learning engine 135. Operating system 110 may then store information gathered from the scan into data store 130, where the information may be retrieved at a later time, synced with cloud-based storage, and the like.

Emotion response service 120 may be configured to handle control of sensors 146a-n and transducers 147a-n to facilitate tracking or administering of emotional stimulation using predefined patterns or series configurations. Stimulation patterns or series may be programmed and executed by a computer running operating system 110 (for example, an embedded processor or system-on-a-chip (SoC) within the eyewear, or a connected computer such as a user's smartphone, tablet, smartwatch, or other user device communicating via a wired connection or a network) to provide proactive stimulation according to preconfigured program instructions, or stimulation may be provided reactively in a dynamic fashion, such as in response to detected emotional (of lack thereof) or cognitive states or in response to environmental cues such as ambient light or music.

Physical tracking engine 125 may be configured to track physical components using sensors 146a-n and transducers 147a-n, for example, tracking engine 125 may track people and orientation of people, environments, lighting, and the like. The tracking information may be used by operating system 110 to provide adjustment parameters to emotion response service 120 to achieve a desired emotional response. Physical tracking engine 125 may also utilize machine learning engine 135 to utilize machine learning in recognition that may be improved over time.

Machine learning engine 135 may be configured as a backend for machine learning that may be tapped into by other components of operating system 105. Machine learning engine 135 may be implemented using any machine learning method commonly used in the art, including, without limitations, neural networks, clustering, reinforcement learning, tree learning, and the like. Machine learning capabilities and efficiently may be improved over time, and may also sync with cloud-based data store 140a, which may enable machine learning engine 135 to share its improvements with a public database, as well as be improved with improvements synced with the public database by other users. Improvements may include, for example, better understanding of a certain facial structure, position of stimuli points, variances between ethnicities, and the like.

Data store 130 may be any form of non-volatile memory commonly used in the art, such as, solid-state memory, flash memory, hard disk drive, and the like. Data store 130 may be configured to store data such as, user identities, user configurations, pre-programmed simulation patterns, pre-scribed emotional therapy regime, and an emotion track that may be programmed for specific use with a particular entertainment title.

Cloud services 140a-n may be used by system 110 to, for example, enable data portability by syncing data from data store 130 with a cloud data store 140a, or move intensive computing tasks to a cloud-based computing resource 140b. Cloud services 140a-n may also include a cloud-based machine learning service 140c, which may be similar to machine learning engine 135, but may be performing machine learning tasks via cloud computing platforms for scalability. Cloud-based machine learning service 140c may be used by device 105 to offload intensive machine learning tasks, for example, when the use of an extensive neural network is required.

Cloud services 140a-n may be configured to sync, and aggregate data from a plurality of enhancement devices. The aggregated data may then be processed using machine learning in order to more efficiently process emotion recognition, emotional stimulus, and the like. The improvements to efficiency may then be easily shared to a plurality of emotion enhancement devices.

Sensors 146 may be configured to detect a user's facial expression, galvanic skin response, brainwave activity, gaze, blink, or other biological indicators of emotion that may be used to then reactively apply stimulation to enhance, counter (for example, to assist a user with depression or another mood disorder, or simply to help alleviate feelings of sadness, fear, anxiety, or other negative emotions), or otherwise direct the user's emotional state. Sensors may also detect environmental factors such as sound or light, altitude, orientation, movement, location, air quality, or other environmental factors that may be used as input for reactively-applied stimulation. For example, chemical sensors could be used to detect the presence or concentration of specific compounds in the air, triggering specific emotional responses based on a scent, pollutant, or other airborne compound.

Transducers 147 may comprise a number of technologies in various combinations and arrangements, for example laser emitters or LEDs that may be used to emit specific frequencies or patterns of light to stimulate skin or bone, motors that may vibrate or "tap" via linear actuation to stimulate skin, muscle, or bone via direct physical contact, electrical contacts that may produce direct-current stimulation (or alternating-current stimulation) to apply to skin and underlying tissues, natural magnets or electromagnets that may be used to provide TMS to tissues. Specific areas have been demonstrated to trigger emotional responses of anger 210a, contempt 210b-c, fear 210d, happiness or joy 210e, sadness 210f, and disgust 210n, however additional research and use may reveal further areas that may elicit similar or additional emotional responses, such as subtler variations and complex emotions such as apprehension or worry. These and other possible forms of stimulation may be applied in various combinations and patterns, for example simultaneously applying light to some target areas and electrical stimulation to others, or applying stimulation to one or more target areas using a pulsating or intermittent pattern, or varying the intensity or form of stimulation such as varying the speed of a motor vibration, the intensity of light, or the electric current being applied. In this manner, various combinations of stimulation as well as various modifications of any particular stimulation or transducer may be employed to achieve desired effects, such as triggering new emotional responses, enhancing emotional responses, or providing therapeutic stimulation such as tDCS or TMS.

In order to compensate for varying physical traits from wearer to wearer, sensors 146 and transducers 147 may be automatically adjusted by operating system 110 based at least in part by tracking information obtained from facial tracking service 115 and physical tracking engine 125. For example, sensors 146 and transducers 147 may utilize microelectronic system technologies that allow the components to reposition using parts on a microscopic scale, or configurable lenses to reposition lights emitted by the transducers to precisely target areas for an expected outcome.

It will be appreciated by one skilled in that art that in some instances, sensors and transducers may be the same component that performs the tasks of sensing and administering emotional stimulation. For clarity, the examples used herein will specify the components separately.

Figure 2:
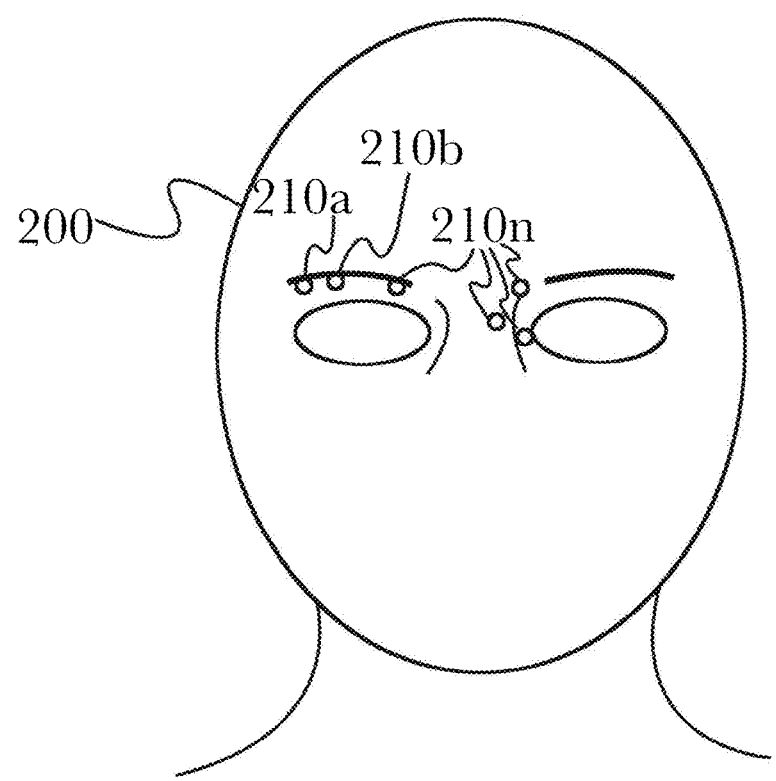
FIG. 2 is a diagram of an exemplary human head, illustrating exemplary areas that elicit emotional response when direct stimulation is applied to the skin.

FIG. 2 is a diagram of an exemplary human head 200, illustrating exemplary areas 210a-n that elicit emotional response when direct stimulation is applied to the skin. There are a number of target areas 210a-n in the human face and scalp that respond to stimulation from electricity, vibration, pressure, or light. When stimulation is applied to skin, bone, or muscle in these areas, specific emotional sensation or sensory experience may be triggered, enabling the direction of a user's emotional response. For example, laser or focused light from an LED may be directed toward specific target areas 210a, 210b to produce an emotional response such as to cause the user to feel anger or contempt. Additionally, it has been demonstrated that using light stimulation in a flashing series of alternate groups of these areas may be used to trigger a surprise response in a user. Using different forms and patterns of stimulation, it becomes possible to direct a user's emotional responses to augment and enhance emotions they may be feeling (for example, for therapeutic uses such as to assist users with reduced emotional response from any of a number of cognitive impairments or injuries), or to produce an emotional response where there was none, such as to directly elicit emotions. For example, emotions may be produced in a user to assist in learning (as it has long been known that emotional states aid in memory storage and recall and assist with the formation of vivid, reliable memories), or to assist a user in skill development such as music or art, where emotion may be a key factor in the creative process. This stimulation may also be used, for example, to elicit or enhance emotions experienced during media consumption or gameplay, for example using a video headset for virtual reality applications (as described below in FIG. 5) to add emotional engagement to a virtual reality game or application, increasing the level of immersion felt by a user.

Detailed Description of Exemplary Aspects

Figure 3:
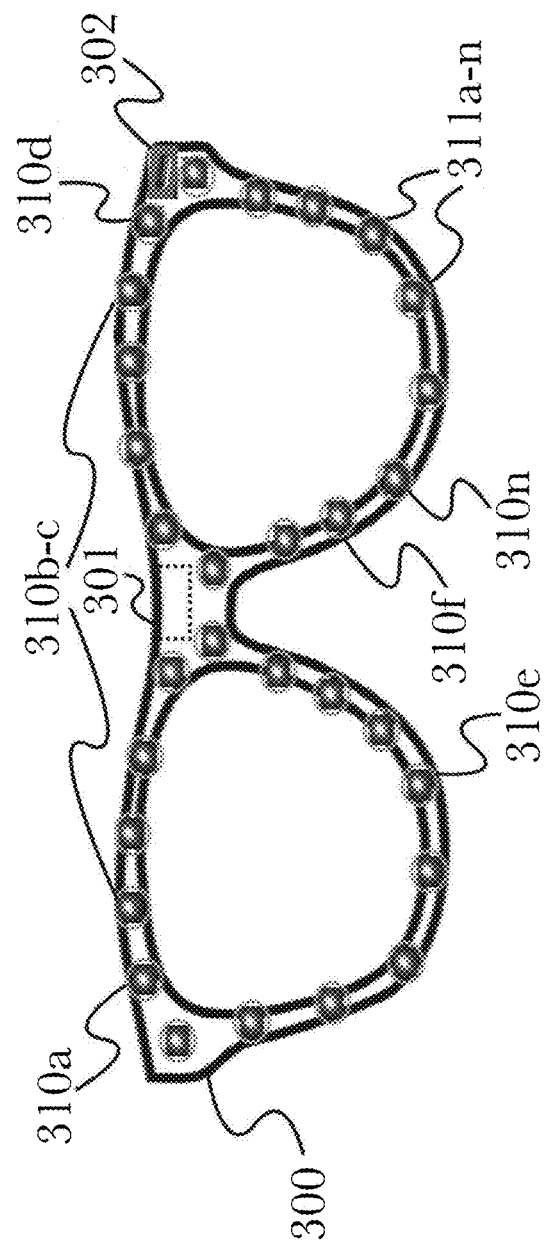
FIG. 3 is a diagram illustrating an exemplary device for inducing emotional response through craniofacial stimulation using eyewear, according to one aspect.

FIG. 3 is a diagram illustrating an exemplary device 300 for inducing emotional response through craniofacial stimulation using eyewear, according to one aspect. According to the aspect, an emotion stimulation device may comprise a set of glasses or similar eyewear 300 such as goggles or a mask (for example, a sleep mask or a protective mask such as may be used in a professional setting, for example construction, laboratory work, medical use, piloting, SCUBA, or other settings where a protective mask or goggles may routinely be worn over the eyes or face) may be configured with a number of stimulation transducers 310a-n and sensors 311a-n, which are discussed in further detail above in FIG. 1. Eyewear 300 may be powered via an internal battery 301 that may either be a disposable primary battery or a rechargeable battery type that may be recharged via various means including (but not limited to) wireless induction or an external charging port 302, or a combination of means such as including both a charging port 302 and internal hardware to support inductive charging. In some embodiments, instead of running operating system 110 on the eyewear, eyewear 300 may connect to an external device that is running operating system 110 via a wireless connection (such as BLUETOOTH, WIFI, cellular network, and the like) or a hard-wired connection.

Figure 4:
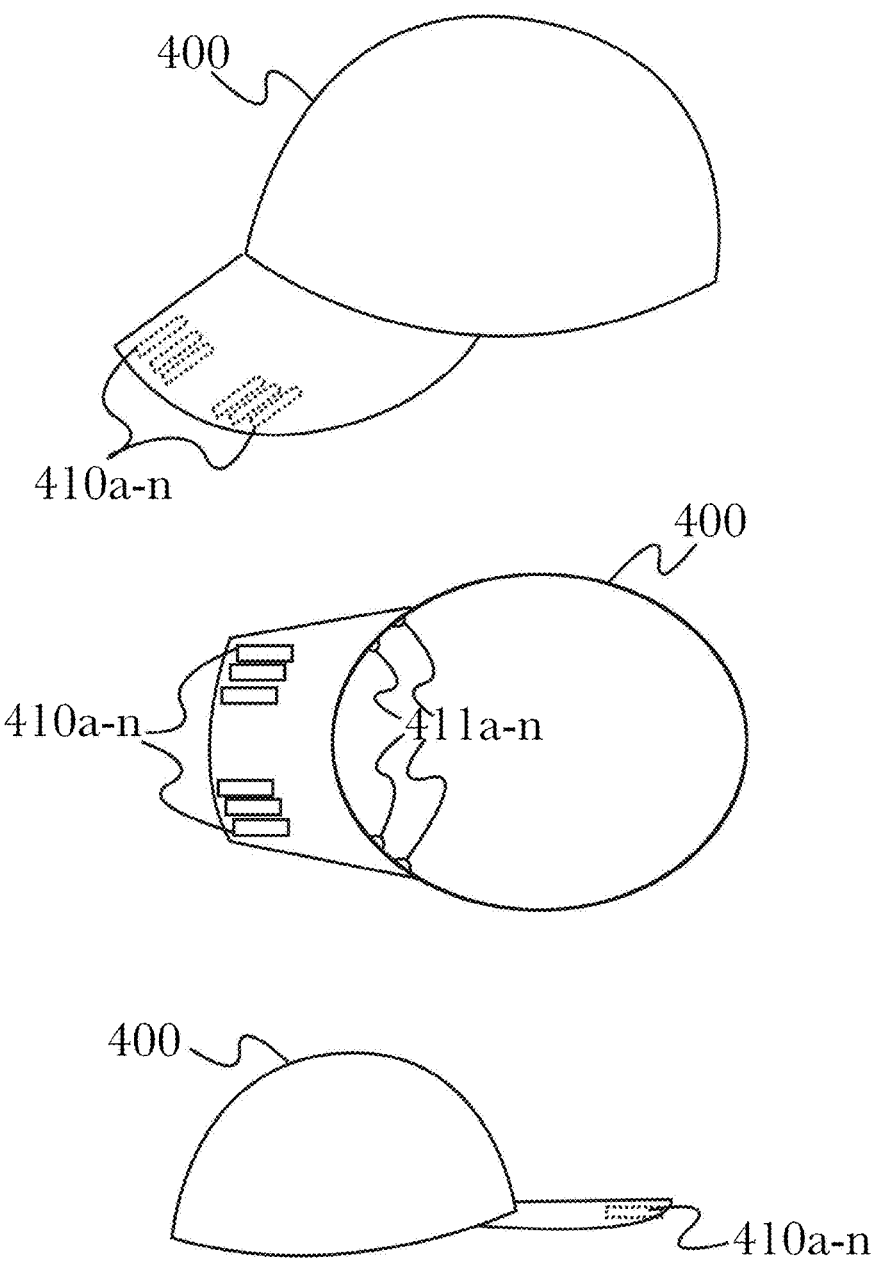
FIG. 4 is a diagram illustrating an exemplary device for inducing emotional response through craniofacial stimulation using headwear, according to one aspect.

FIG. 4 is a diagram illustrating an exemplary device 400 for inducing emotional response through craniofacial stimulation using headwear, according to one aspect. According to the aspect, an emotion stimulation device may comprise a hat 400 or other headwear such as a mask or helmet may be configured with a plurality of transducers 410*a-n* and sensors 411*a-n* to provide proactive or reactive stimulation to a user's face and scalp. As with eyewear 300 (described above with reference to FIG. 3), transducers may comprise a number of technologies in various combinations and arrangements, for example laser emitters or LEDs that may be used to emit specific frequencies or patterns of light to stimulate skin or bone, motors that may vibrate or "tap" via linear actuation to stimulate skin, muscle, or bone via direct physical contact, electrical contacts that may produce direct-current stimulation (or alternating-current stimulation) to apply to skin and underlying tissues, natural magnets or electromagnets that may be used to provide TMS to tissues; as well as read the emotional status of a wearer. Headwear 400 may be powered via an internal battery that may either be a disposable primary battery or a rechargeable battery type that may be recharged via various means including (but not limited to) wireless induction or an external charging port, or a combination of means such as including both a charging port and internal hardware to support inductive charging. In some embodiments, instead of running operating system 110 on the headwear, headwear 400 may connect to an external device that is running operating system 110 via a wireless connection (such as BLUETOOTH, WIFI, cellular network, and the like) or a hard-wired connection.

Figure 5:
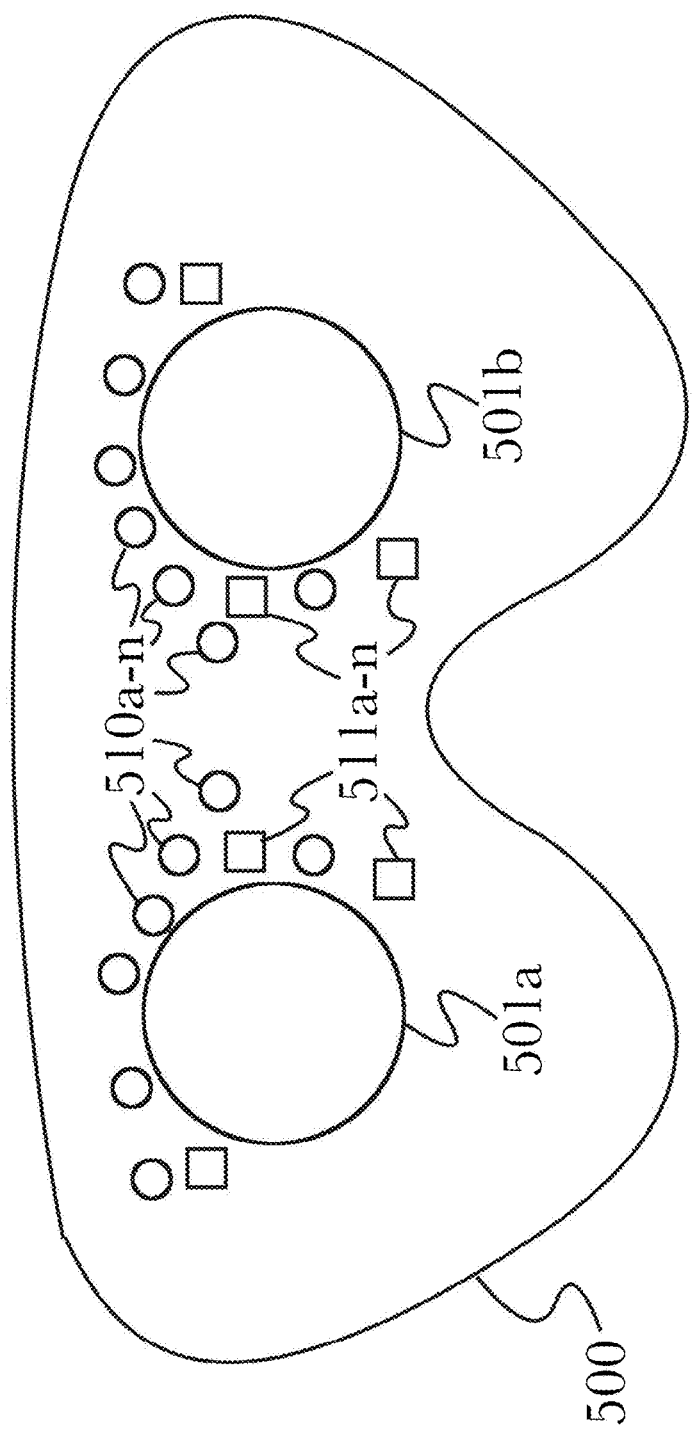
FIG. 5 is a diagram illustrating an exemplary device for inducing emotional response through craniofacial stimulation using a video headset, according to one aspect.

FIG. 5 is a diagram illustrating an exemplary device 500 for inducing emotional response through craniofacial stimulation using a video headset, according to one aspect. According to the aspect, an emotion stimulation device may comprise a video headset 500 such as private video viewing glasses or a virtual reality headset may be configured with a plurality of transducers 510*a-n* or sensors 511*a-n* positioned about eye holes, screens, or viewing ports 501*a-b* to provide proactive or reactive stimulation to a user's face and scalp. As with eyewear and headwear (described above with reference to FIG. 3 and FIG. 4), transducers may comprise a number of technologies in various combinations and arrangements, for example laser emitters or LEDs that may be used to emit specific frequencies or patterns of light to stimulate skin or bone, motors that may vibrate or "tap" via linear actuation to stimulate skin, muscle, or bone via direct physical contact, electrical contacts that may produce direct-current stimulation (or alternating-current stimulation) to apply to skin and underlying tissues, natural magnets or electromagnets that may be used to provide TMS to tissues; as well as read the emotional status of a wearer. Video headset 500 may be powered via an internal battery that may either be a disposable primary battery or a rechargeable battery type that may be recharged via various means including (but not limited to) wireless induction or an external charging port, or a combination of means such as including both a charging port and internal hardware to support inductive charging. In some embodiments, instead of running operating system 110 on the video headset, video headset 500 may connect to an external device that is running operating system 110 via a wireless connection (such as BLUETOOTH, WIFI, cellular network, and the like) or a hard-wired connection.

Figure 6:
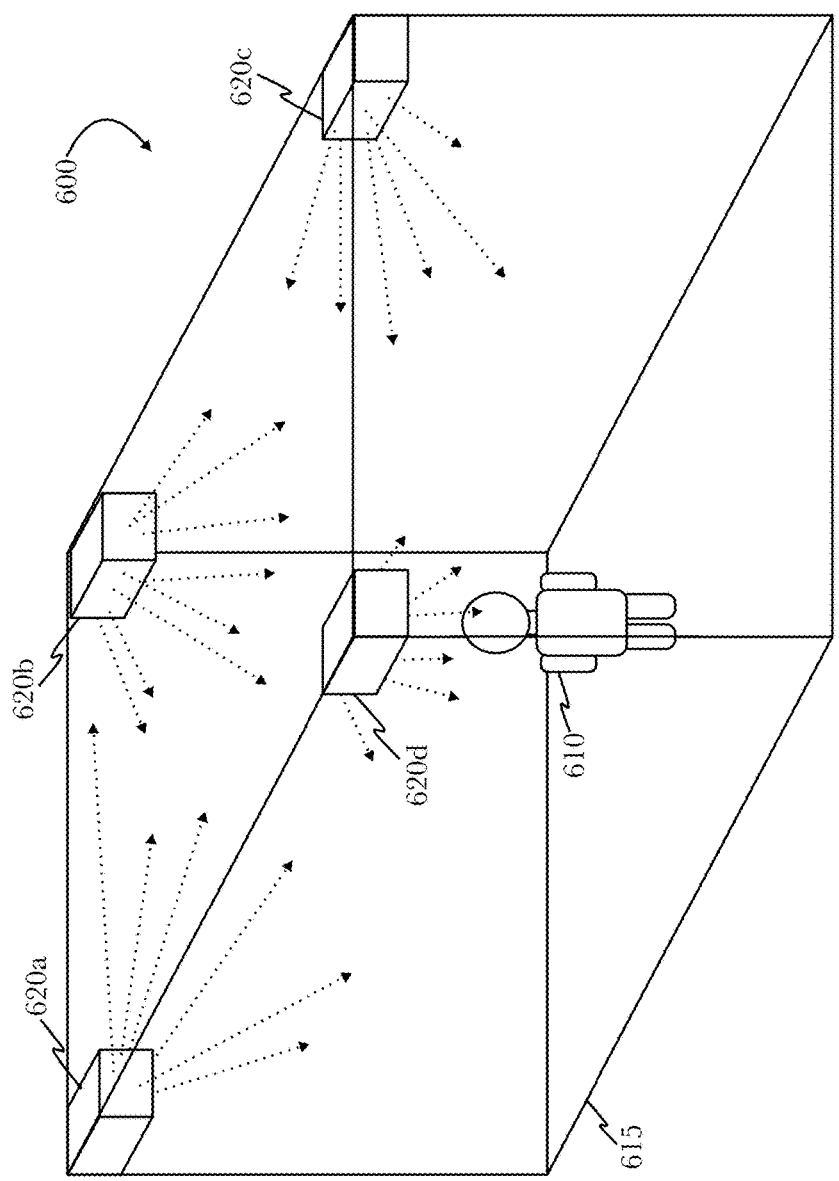
FIG. 6 is a simplified diagram of an exemplary system utilizing transducers not attached to the body to stimulate or control emotional states, according to one aspect.

FIG. 6 is a diagram illustrating an exemplary system 600 for inducing emotional response through craniofacial stimulation using a plurality of room-mounted transducers and sensors, according to one aspect. System 600 shows a plurality of transducers and sensor assemblies 620*a-d* similar to those found in eyewear 300, headwear 400, or a headset 500 (as described above, with reference to FIGS. 3-5); and installed around a room 615. The assemblies may also use the same operational methods for the transducers and sensors found in eyewear 300, headwear 400, or a headset 500. Assemblies 620*a-d* may operate independently and sync with each other via a wireless connection (such as BLUETOOTH or WIFI) or a hard-wired connection, or may connect to a common computing system running operating system 110. Assemblies 620*a-d* may be configured to track a user 610 as the user moves around room 615, and simultaneously stimulate or control the emotional state of user 610 without being required to wear any hardware on their body. On-the-fly adjustments may also be made by system 110 if obstructions or changes in orientation are detected using assemblies 620*a-d*. In some embodiments, instead of running system 110 on the transducer and sensor assemblies, assemblies 620*a-d* may connect to an external device that is running system 110 via a wireless connection (such as BLUETOOTH, WIFI, cellular network, and the like) or a hard-wired connection.

It should be understood that although the illustration found in FIG. 6 shows a single user in a single room, this is not indicative of any limitations of the present invention. Other embodiments may, for example, have transducer assemblies installed throughout an entire house or facility, and the assemblies may be configured to track and administer emotional stimulation simultaneously to a plurality of users.

Figure 7:
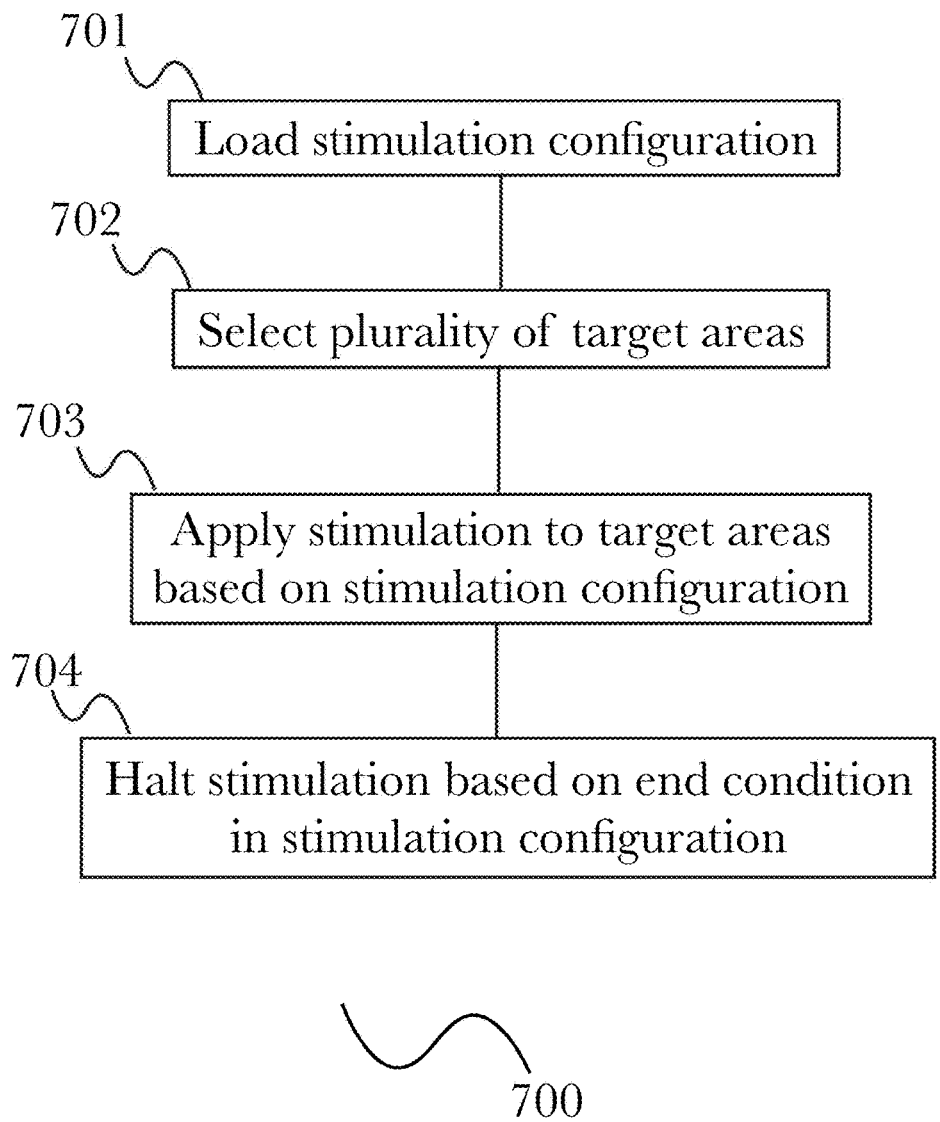
FIG. 7 is a flow diagram illustrating an exemplary method for inducing emotional response through craniofacial stimulation to elicit a specific emotional response, according to one aspect.

FIG. 7 is a flow diagram illustrating an exemplary method 700 for inducing emotional response through craniofacial stimulation to elicit a specific emotional response, according to one aspect. In an initial step 701, an emotion enhancement device, such as one described above with reference to FIGS. 3-6, may load a preconfigured stimulation configuration based on a desired emotional response, for example a preprogrammed pattern or sequence of specific stimulation such as (for example) applying light of specific wavelength and intensity, or applying vibration or pressure of specific intensity. The configuration may also contain information pertaining to physical dimensions of a particular user gathered by the facial tracking service. The emotion stimulation device may optionally be connected (for example, via a wired connection or via a communication network) to a user device such as a smartphone, tablet, wearable computing device, or other device that may monitor user emotional response and direct the emotion enhancement device (thereby moving any processing operations and associated hardware and software needs to an external device, for example for ease of design or use of the emotion stimulation device or so that a single emotion enhancement device may be used with multiple user devices, such as to share among multiple users or accommodate a user replacing their phone, or to enable control of the emotion enhancement device via a software application operating on a user device). A plurality of target areas may then be selected at step 702, to which the selected stimulation may then be applied at step 703. A selected stimulation program may optionally include duration information, so that after a predefined period of time (or other end condition, such as after performing a certain number of iterations of a stimulation pattern, or after the desired emotional response is detected via hardware sensors, for example) stimulation may be halted at step 704 either gradually in a "ramp-down" fashion or immediately (as may be appropriate if a problem is detected such as if the stimulation is eliciting the wrong emotional response or the user presses a "stop" button within a control application on their device, for example).

Figure 8:
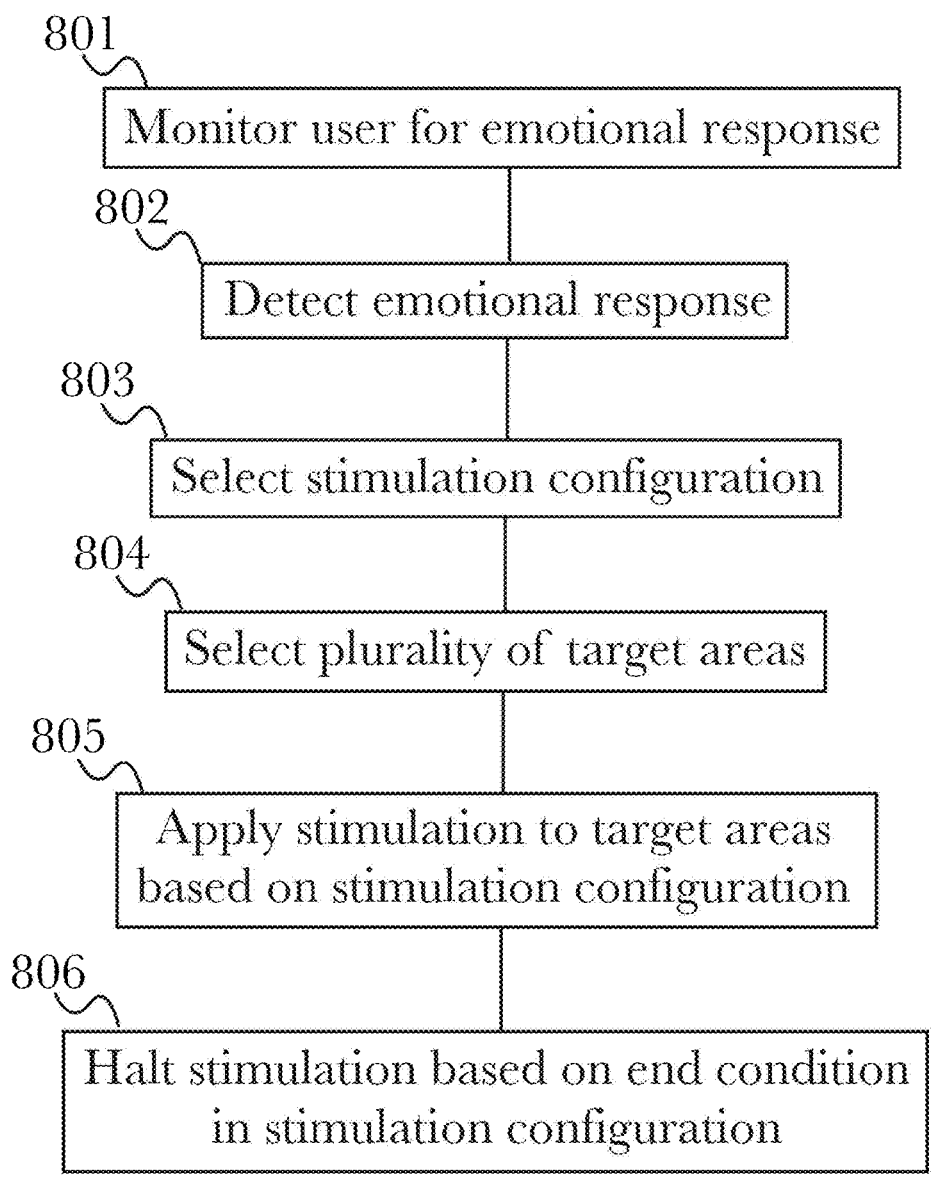
FIG. 8 is a flow diagram illustrating an exemplary method for inducing emotional response through craniofacial stimulation in response to a user's current emotional state, according to one aspect.

FIG. 8 is a flow diagram illustrating an exemplary method 800 for inducing emotional response through craniofacial stimulation in response to a user's current emotional state, according to one aspect. In an initial step 801, an emotion enhancement device, such as one described above with reference to FIGS. 3-6, may monitor a user for emotional response such as (for example) by utilizing a plurality of hardware sensors to detect user behaviors such as facial expressions, posture, movement, or other metrics. The emotion stimulation device may optionally be connected (for example, via a wired connection or via a communication network) to a user device such as a smartphone, tablet, wearable computing device, or other device that may monitor user emotional response and direct the emotion enhancement device (thereby moving any monitoring operations and associated hardware and software needs to an external device, for example for ease of design or use of the emotion stimulation device or so that a single emotion enhancement device may be used with multiple user devices, such as to share among multiple users or accommodate a user replacing their phone, or other such uses). In a next step 802, an emotional response may be detected, for example by recognizing specific movements or expressions, or by detecting changes in specific biometric readings such as (for example, including but not limited to) heart rate, heart rate variability, galvanic skin response, or pupil dilation, using the transducers or monitoring hardware sensors. In a next step 803, a stimulation configuration may be selected, for example a preprogrammed pattern or sequence of specific stimulation such as (for example) applying light of specific wavelength and intensity, or applying vibration or pressure of specific intensity. A plurality of target areas may then be selected at step 804, to which the selected stimulation may then be applied at step 805. This may be used to optionally heighten a user's emotional response, for example to amplify feelings of joy or to amplify a fear response (for example, during a game, film, or other interactive experience where fear is an intended part of the experience), or this may be used to counteract or suppress a user's emotional response, for example to help suppress feelings of fear or anxiety, such as in a therapeutic use. A selected stimulation program may optionally include duration information, so that after a predefined period of time (or other end condition, such as after performing a certain number of iterations of a stimulation pattern, or after the desired emotional response is detected via hardware sensors, for example) stimulation may be halted 806 either gradually in a "ramp-down" fashion or immediately (as may be appropriate if a problem is detected such as if the stimulation is eliciting the wrong emotional response or the user presses a "stop" button within a control application on their device, for example).

Figure 9:
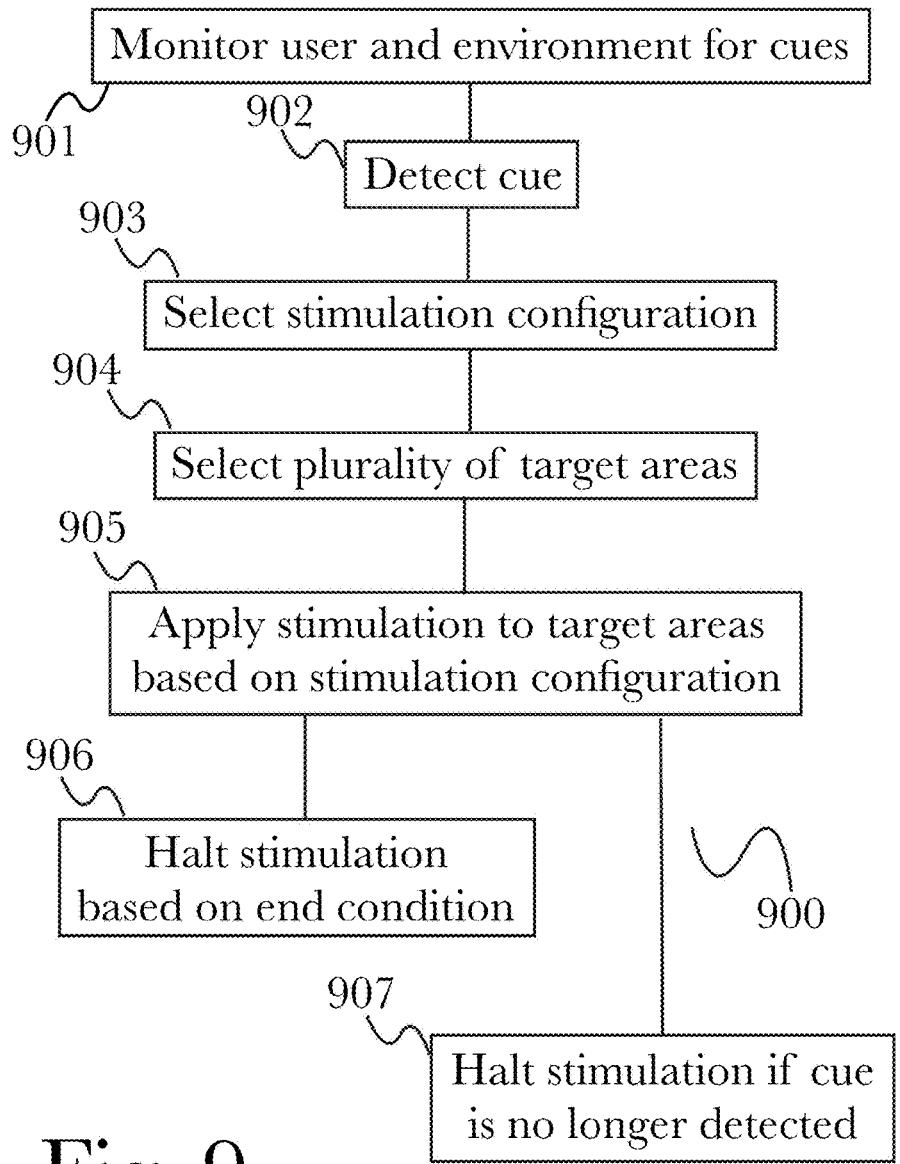
FIG. 9 is a flow diagram illustrating an exemplary method for inducing emotional response through craniofacial stimulation using reactive stimulation in response to sensor input, according to one aspect.

FIG. 9 is a flow diagram illustrating an exemplary method 900 for inducing emotional response through craniofacial stimulation using reactive stimulation in response to sensor input, according to one aspect. In an initial step 901, an emotion enhancement device, such as one described above with reference to FIGS. 3-6, may monitor a user and environment for input cues, such as (for example) by utilizing a plurality of hardware sensors or transducers to detect user behaviors such as facial expressions, posture, movement, or other metrics. The emotion stimulation device may optionally be connected (for example, via a wired connection or via a communication network) to a user device such as a smartphone, tablet, wearable computing device, or other device that may monitor user emotional response and direct the emotion enhancement device (thereby moving any monitoring operations and associated hardware and software needs to an external device, for example for ease of design or use of the emotion stimulation device or so that a single emotion enhancement device may be used with multiple user devices, such as to share among multiple users or accommodate a user replacing their phone, or other such uses). In a next step 902, a cue may be detected by a sensor, whether from a user (for example, a spoken utterance from a user, or a facial expression or biometric response as described previously in FIG. 8) or from the environment (such as, for example, a specified frequency or intensity of ambient light or sound). In a next step 903, a stimulation configuration may be selected based on the received sensor input, for example specific ambient light may always trigger a specific light-based stimulation in response (for example, to counteract or amplify mood-induced changes based on lighting). A plurality of target areas may then be selected at step 904, to which the selected stimulation may then be applied at step 905 until either a predefined end condition is met at step 906, or the sensor no longer detects the trigger condition at step 907.

Figure 10:
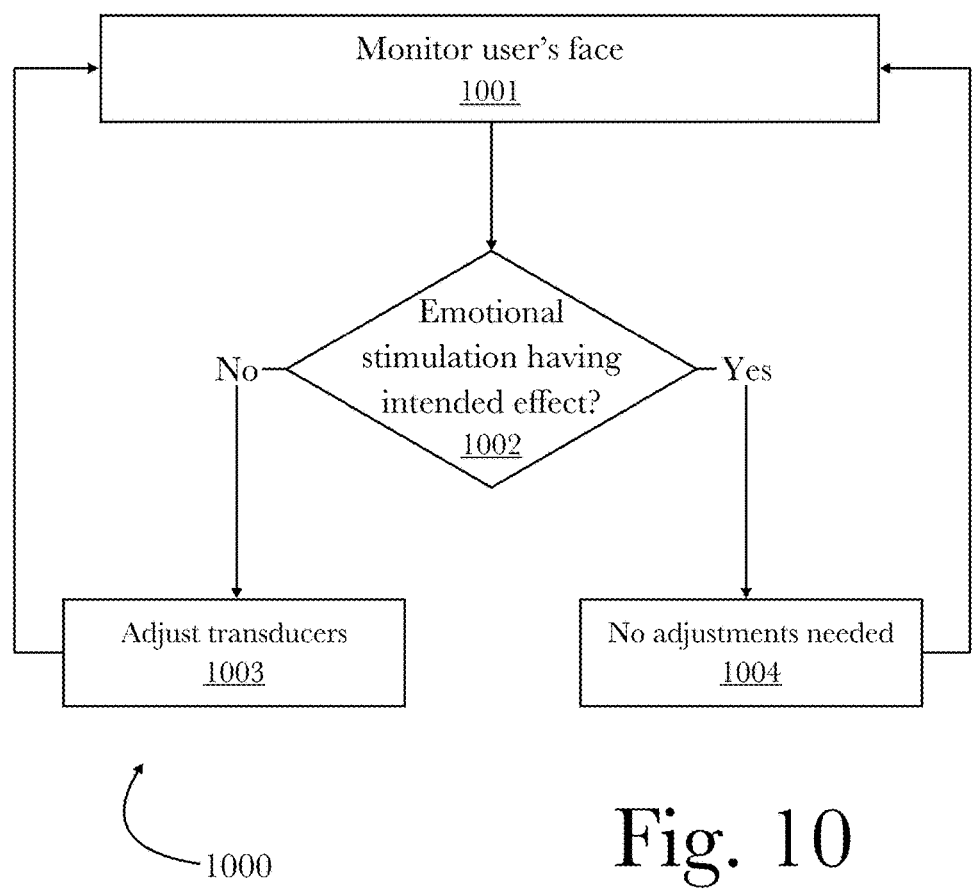
FIG. 10 is a flow diagram illustrating an exemplary method for on-the-fly adjustments for emotion stimulation, according to one aspect.

FIG. 10 is a flow diagram illustrating an exemplary method 1000 for on-the-fly adjustments for emotion stimulation, according to one aspect. At an initial step 1001, an emotion enhancement device, such as one described above with reference to FIGS. 3-6, may scan a user's face using onboard sensors. The purpose of the scan is for operating system 110 to determine whether an emotional stimulation configuration is having the desired effect. At decision block 1002, if the system determines that the desired effect has not been sufficiently achieved, the system automatically adjusts configuration for the transducers at step 1003. This may include, for example, increasing stimulation intensity if the effect strength appears too weak or adjusting the positioning of the transducer to provide stimulation to another area of the user's face if the stimulation points are misaligned with the transducers. On the other hand, if at decision block 1002, the intended effect is in place, then the system makes no adjustments at step 1004.

It should be appreciated that the method described in FIG. 10 may be on ongoing process, so that the system can provide a predictable experience to the user in cases where there may be environmental factors that may affect how well the emotional stimulation is working, for example, when using a room-based system where several people may be present that may act as obstacles between transducers and intended target of the emotional stimulation.

Figure 11:
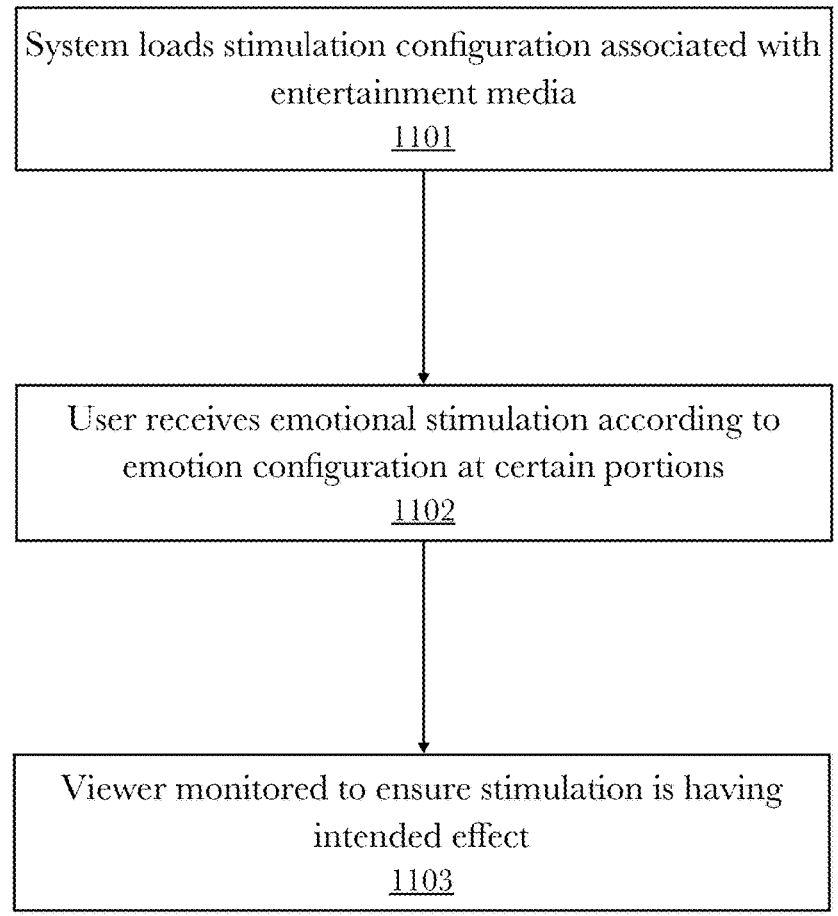
FIG. 11 is a flow diagram illustrating an exemplary method for inducing emotional response through craniofacial stimulation in accordance with a configuration associated with a piece of entertainment, according to one aspect.

FIG. 11 is a flow diagram illustrating an exemplary method 1100 for inducing emotional response through craniofacial stimulation in accordance with a configuration associated with a piece of entertainment, according to one aspect. At in initial step 1101, a stimulation configuration associated with a piece of entertainment is loaded by operating system 110, for example, music, movies, video games, and the like which has been programmed specifically for that particular piece of entertainment by creators of said piece of entertainment. At step 1102, during certain parts during the piece of entertainment, the user may receive emotional stimulation based on the provided stimulation configuration to elicit a certain emotion from the user intended by its creators to maximize the emotional response for a certain sequence. Stimulation may be provided to users using their own individual stimulation device, for instance, when using embodiments shown in FIG. 3-5; or stimulation may be provided for an entire room or theater, such as the embodiment shown in FIG. 6. At step 1103, the user or users are actively monitored according to the method described in FIG. 10 to ensure the stimulation is have the desired effect, and, if necessary, adjustments may be made.

Figure 12:
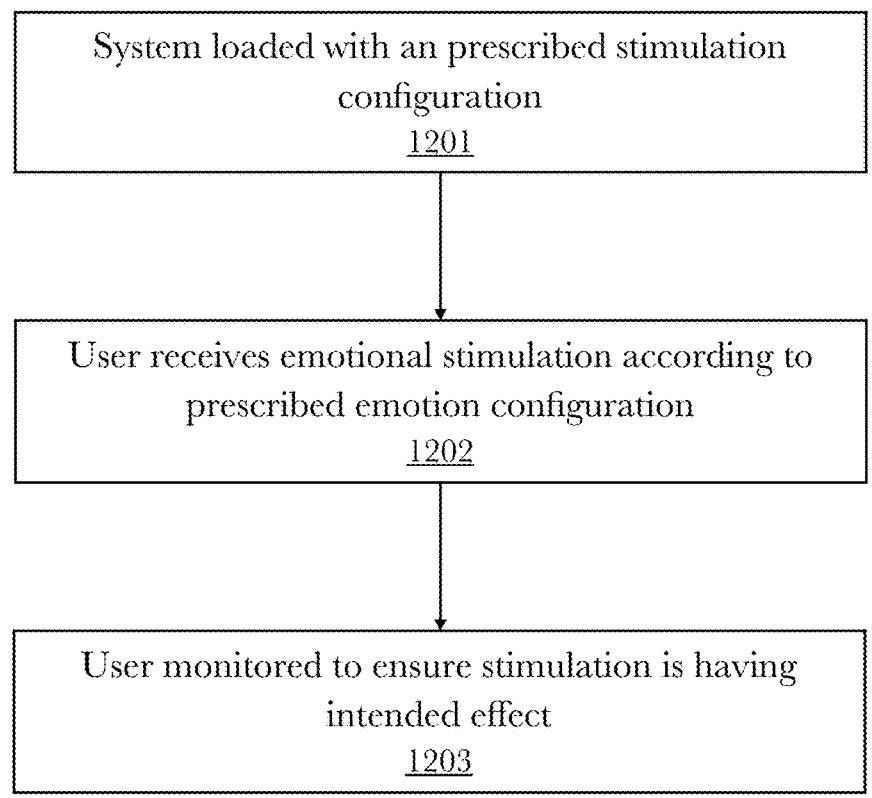
FIG. 12 is a flow diagram illustrating an exemplary method for inducing emotional response through craniofacial stimulation for emotional therapy, according to one aspect.

FIG. 12 is a flow diagram illustrating an exemplary method 1200 for inducing emotional response through craniofacial stimulation for emotional therapy, according to one aspect. At an initial step 1201, a prescribed emotional stimulation configuration may be loaded by the system. This may be, for example, a configuration to elicit feelings of happiness to treat depression, or calmness to treat stress or post-traumatic stress disorder. At step 1202, the prescribed stimulation regiment may be administered to the user, for instance, through any of the embodiments shown in FIG. 3-6. The regiment may entail, for example, a session that lasts for a prespecified time duration or various emotional states may be cycled through. At step 1203, the user or users are actively monitored according to the method described in FIG. 10 to ensure the stimulation is have the desired effect, and, if necessary, adjustments may be made.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 13:
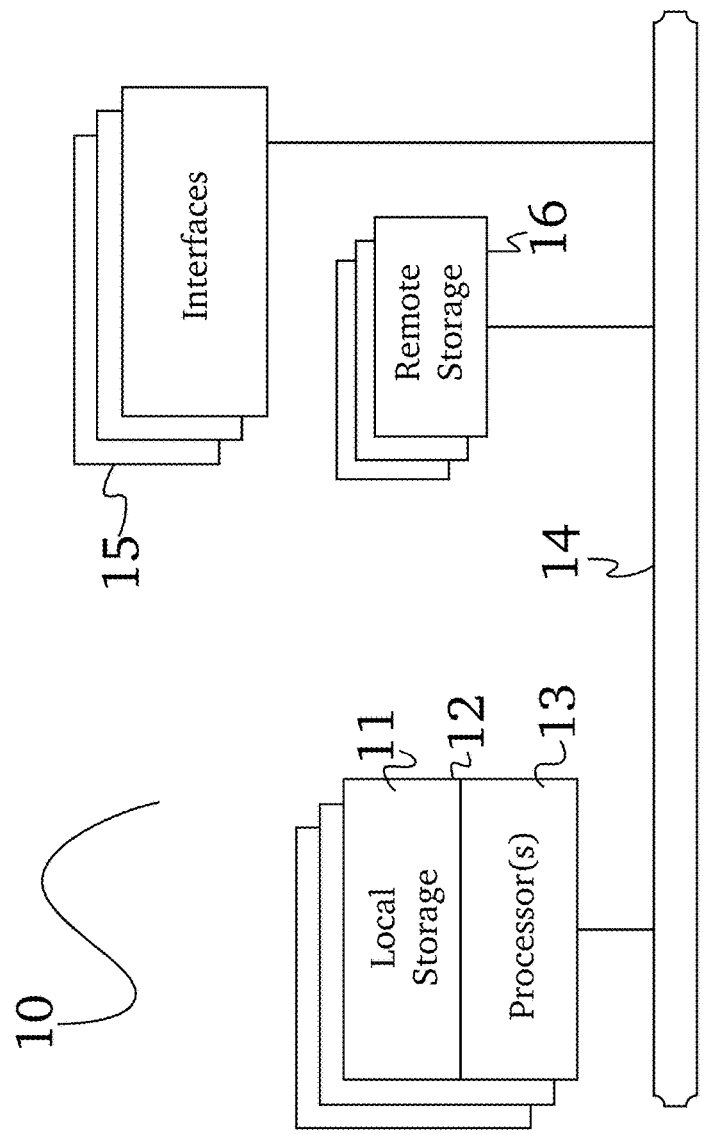
FIG. 13 is a block diagram illustrating an exemplary hardware architecture of a computing device used in various embodiments of the invention.

Referring now to FIG. 13, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/N hardware interfaces) and, in some instances, volatile and/or non-volatile memory (e.g., RAM).

Although the system shown in FIG. 13 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 14:
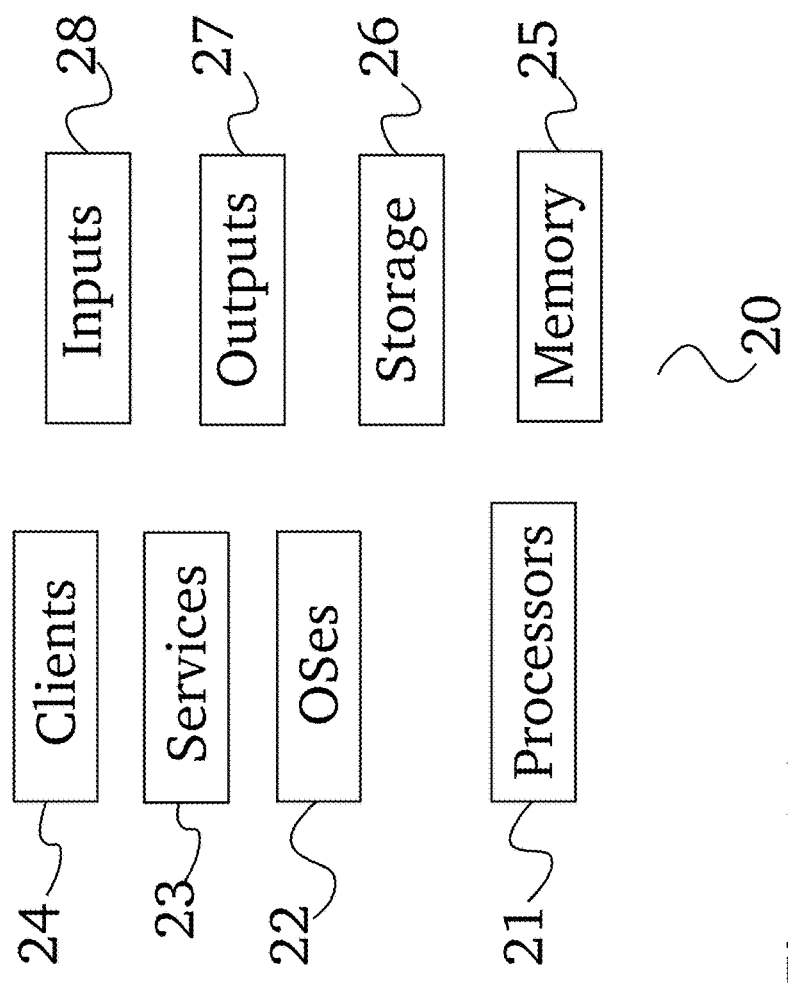
FIG. 14 is a block diagram illustrating an exemplary logical architecture for a client device, according to various embodiments of the invention.

In some aspects, systems may be implemented on a standalone computing system. Referring now to FIG. 14, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 13). Examples of storage devices 26 include flash memory, magnetic hard drive, CD-ROM, and/or the like.

Figure 15:
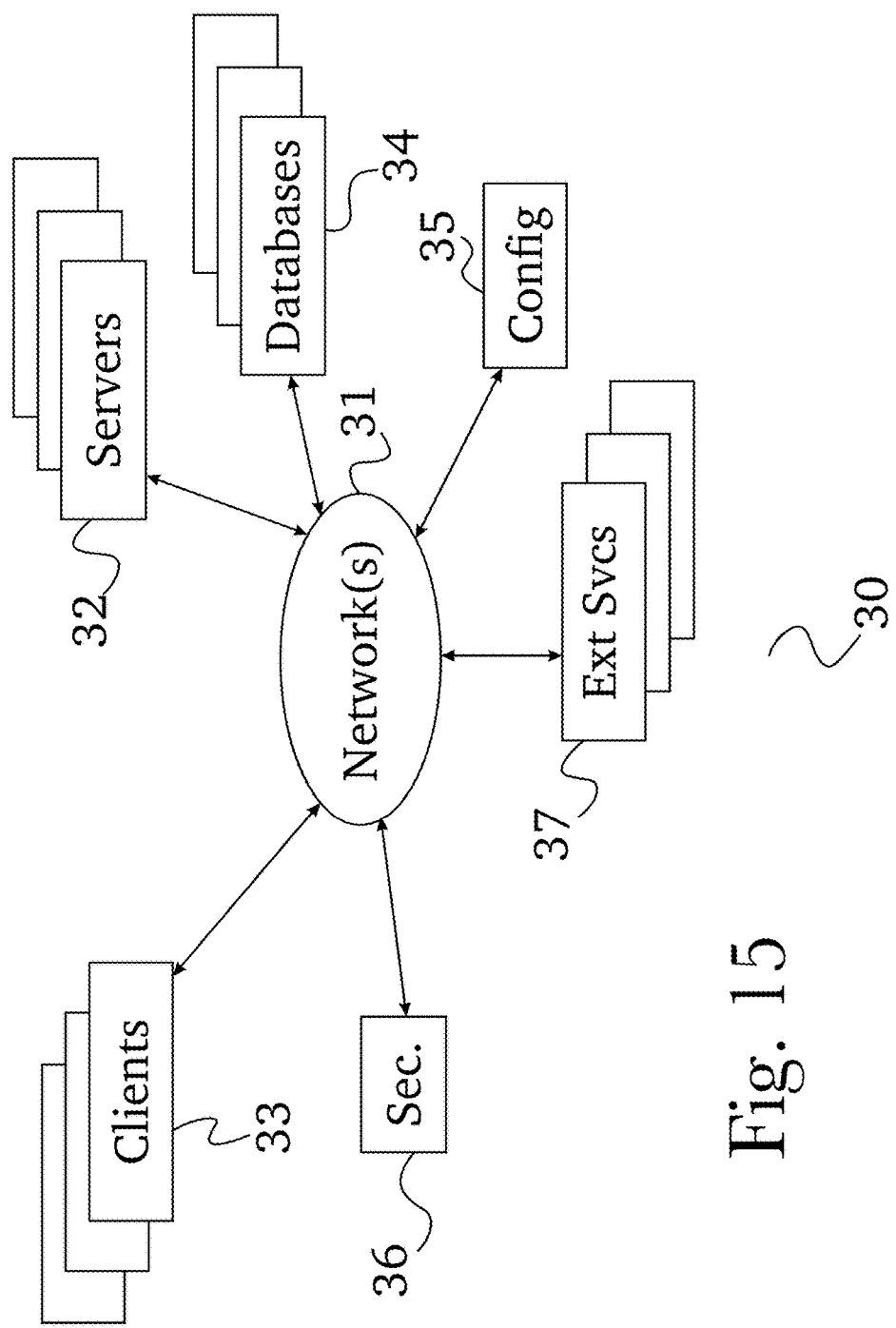
FIG. 15 is a block diagram illustrating an exemplary architectural arrangement of clients, servers, and external services, according to various embodiments of the invention.

In some aspects, systems may be implemented on a distributed computing network, such as one having any number of clients and/or servers. Referring now to FIG. 15, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 14. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some aspects, clients 33 or servers 32 (or both) may make use of one or more specialized services or appliances that may be deployed locally or remotely across one or more networks 31. For example, one or more databases 34 may be used or referred to by one or more aspects. It should be understood by one having ordinary skill in the art that databases 34 may be arranged in a wide variety of architectures and using a wide variety of data access and manipulation means. For example, in various aspects one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 16:
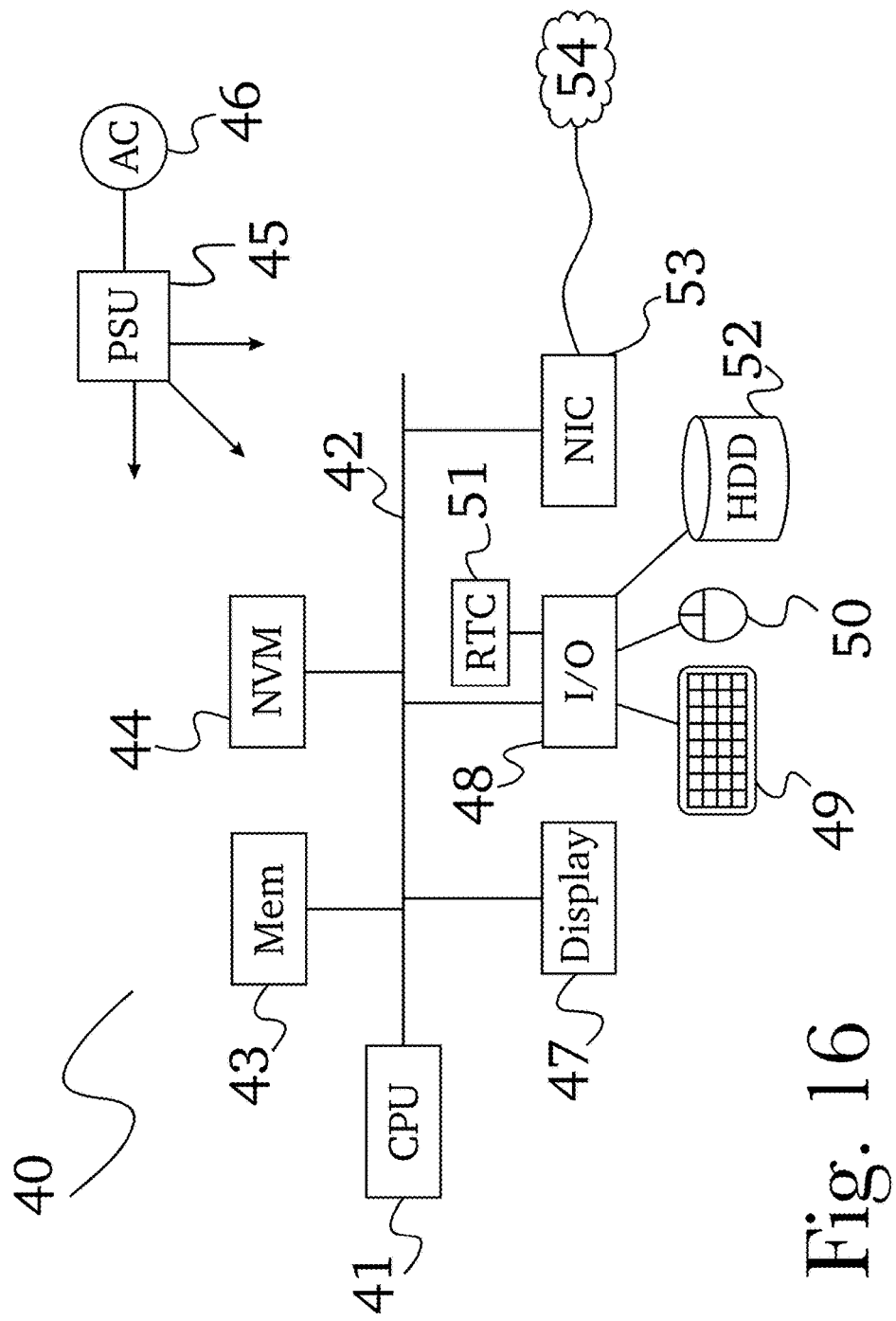
FIG. 16 is another block diagram illustrating an exemplary hardware architecture of a computing device used in various embodiments of the invention.

FIG. 16 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

It will be appreciated that various aspects may improve the performance of emotion tracking and/or emotion stimulation, according to the invention. For example, in a preferred aspect, light emitted by transducers will be insensible (i.e., invisible) to a receiving user. This may be accomplished either by using very weak optical irradiation at target locations on a user's face, such that the light emitted is not visible to the user. Alternatively, or in addition, non-visible wavelengths may be used, which are nevertheless known to be effective in stimulating desired emotional responses in humans. For example, infrared or near-infrared light may be transmitted by transducers in order to stimulate specific emotional responses in a user without displaying any visible light to the user.

The skilled person will be aware of a range of possible modifications of the various aspects described above. Accordingly, the present invention is defined by the claims and their equivalents.

What is claimed is:

1. A system for inducing emotional response through craniofacial stimulation, comprising:
    an article of headgear further comprising:
        one or more hardware sensors configured to detect environmental conditions near the article of headgear; and
        one or more stimulation transducers being arranged to correspond to a plurality of target areas about the face and head of a human user when the headwear is worn, wherein the plurality of stimulation transducers is configured to apply direct stimulation to the plurality of target areas; and
    an emotion enhancement device comprising: a processor, a memory, and a plurality of programming instructions stored in the memory and operating on the processor, wherein the programming instructions, when operating on the processor, cause the processor to:
receive a signal from each of the one or more hardware sensors;
select a stimulation configuration based on a combination of the signals received from the one or more hardware sensors;
continuously adjust the stimulation configuration based on the combination of signals from the one or more hardware sensors;
select a plurality of target areas about a user's face and head based at least in part on the adjusted stimulation configuration;
direct the operation of a plurality of stimulation transducers based at least in part on the adjusted stimulation configuration; and
apply stimulation to a plurality of target areas about a user's face and head, the target areas being selected based on the adjusted stimulation configuration.

2. The system of claim 1, wherein the stimulation transducers comprise a laser emitter.

3. The system of claim 1, wherein the stimulation transducers comprise a light-emitting diode.

4. The system of claim 1, wherein the stimulation transducers transmit light to specific areas of a user's face.

5. The system of claim 4, wherein the light transmitted is invisible to the user.

6. The system of claim 5, wherein the light transmitted is in the infrared or near-infrared band.

7. The system of claim 1, wherein the headgear is configured to be worn on the face of a human user.

8. The system of claim 7, wherein the headgear comprises a pair of goggles.

9. The system of claim 7, wherein the headgear comprises a hat.

10. The system of claim 7, wherein the headgear comprises a virtual reality headset.

11. The system of claim 7, wherein the emotion enhancement device comprises room-installed transducer and sensor assemblies.

12. The system of claim 1, further comprising a plurality of hardware sensors arranged about the emotion enhancement device, wherein the plurality of hardware sensors is configured to provide a plurality of sensor input cues to the processor.

13. The system of claim 12, wherein the stimulation configuration is selected based at least in part on the plurality of sensor input cues.

14. A method for inducing emotional response through craniofacial stimulation, comprising the steps of:
placing an article of headgear on the head of a user, the article of headgear comprising:
one or more hardware sensors configured to detect environmental conditions near the article of headgear;
one or more stimulation transducers being arranged to correspond to a plurality of target areas about the face and head of a human user when the headwear is worn, wherein the plurality of stimulation transducers is configured to apply direct stimulation to the plurality of target areas; and
operating the article of headgear using an emotion enhancement device by:
receiving a signal from each of the one or more hardware sensors;
selecting a stimulation configuration based on a combination of the signals received from the one or more hardware sensors;
continuously adjusting the stimulation configuration based on the combination of signals from the one or more hardware sensors;
selecting a plurality of target areas about a user's face and head based at least in part on the adjusted stimulation configuration;
directing the operation of a plurality of stimulation transducers based at least in part on the adjusted stimulation configuration; and
applying stimulation to a plurality of target areas about a user's face and head, the target areas being selected based on the adjusted stimulation configuration.

15. The method of claim 14, further comprising the steps of:
(e) receiving a plurality of input cues from a plurality of hardware sensors positioned about the emotion enhancement device; and
(f) selecting a stimulation configuration based at least in part on the plurality of input cues.

16. A method for automated adjustment of a craniofacial stimulation emotional response, comprising the steps of:
receiving a plurality of input cues from a plurality of hardware sensors positioned about an emotion enhancement device, the hardware sensors configured to detect environmental conditions near the article of headgear, and the emotion enhancement device comprising a plurality of stimulation transducers arranged about an article of headwear;
select a stimulation configuration based on a combination of the signals received from the one or more hardware sensors;
continuously adjust the stimulation configuration based on the combination of signals from the one or more hardware sensors;
apply stimulation through the stimulation transducers to a plurality of target areas about a user's face and head, the target areas being selected based on the adjusted stimulation configuration.

17. The method of claim 16, wherein adjustments are saved separately for each unique user.

* * * * *